(12) United States Patent
Ramirez

(10) Patent No.: US 12,714,457 B2
(45) Date of Patent: Aug. 25, 2026

(54) ATHERECTOMY CATHETERS HAVING MOVABLE BEADS

(71) Applicant: BARD PERIPHERAL VASCULAR, INC., Franklin Lakes, NJ (US)

(72) Inventor: Ruben Ramirez, Mesa, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 111 days.

(21) Appl. No.: 18/860,181

(22) PCT Filed: May 24, 2022

(86) PCT No.: PCT/US2022/030654
§ 371 (c)(1),
(2) Date: Oct. 25, 2024

(87) PCT Pub. No.: WO2023/229577
PCT Pub. Date: Nov. 30, 2023

(65) Prior Publication Data

US 2025/0288315 A1 Sep. 18, 2025

(51) Int. Cl.
*A61B 17/3207* (2006.01)
*A61B 17/00* (2006.01)
(Continued)

(52) U.S. Cl.
CPC ................ *A61B 17/320758* (2013.01); *A61B 17/00234* (2013.01); *A61B 90/03* (2016.02); *A61B 2017/00017* (2013.01); *A61B 2017/00238* (2013.01); *A61B 2017/00305* (2013.01); *A61B 2017/00561* (2013.01);
(Continued)

(58) Field of Classification Search
CPC .............. A61B 17/22; A61B 17/22004; A61B 17/22012; A61B 17/2202; A61B 17/320068; A61B 17/3207; A61B 17/320758; A61B 2017/22014; A61B 2017/22015; A61B 2017/22079;
(Continued)

(56) References Cited

U.S. PATENT DOCUMENTS 5,312,427 A * 5/1994 Shturman ............ A61M 25/01 606/159
5,925,055 A * 7/1999 Adrian .............. A61B 17/2202 606/171
(Continued)

FOREIGN PATENT DOCUMENTS

DE 10146011 A1 6/2012

OTHER PUBLICATIONS

International Search Report and Written Opinion for Appln. No. PCT/US2022/030654, mailed Jan. 30, 2023, 18 pages.

*Primary Examiner* — Diane D Yabut
*Assistant Examiner* — Christian D Knauss
(74) *Attorney, Agent, or Firm* — Dinsmore & Shohl LLP

(57) ABSTRACT

An atherectomy catheter for performing an atherectomy procedure, the atherectomy catheter includes a catheter body defining one or more lumens, a core wire extending through a core wire lumen of the one or more lumens of the catheter body, and an abrasive bead slidably mounted to the core wire. The core wire is configured to be coupled to an excitation device and operation of the excitation device causes the abrasive bead to rotate about and slide longitudinally along the core wire.

20 Claims, 6 Drawing Sheets

(51) Int. Cl.
*A61B 90/00* (2016.01)
*A61B 17/32* (2006.01)

(52) U.S. Cl.
CPC ............... *A61B 2017/00845* (2013.01); *A61B 2017/320004* (2013.01); *A61B 2090/034* (2016.02); *A61B 2217/005* (2013.01)

(58) Field of Classification Search
CPC ....... A61B 2017/320004; A61B 2017/320766; A61B 2017/320775
See application file for complete search history.

(56) References Cited

U.S. PATENT DOCUMENTS

| | | | | |
|---|---|---|---|---|
| 6,299,623 | B1 * | 10/2001 | Wulfman ....... | A61B 17/320758 606/159 |
| 6,554,846 | B2 | 4/2003 | Hamilton et al. | |
| 8,192,451 | B2 | 6/2012 | Cambronne et al. | |
| 9,757,144 | B2 | 9/2017 | Shturman | |
| 9,936,970 | B2 | 4/2018 | Higgins | |
| 10,299,820 | B2 | 5/2019 | Kohler et al. | |
| 11,147,582 | B2 | 10/2021 | Kallok et al. | |
| 2014/0180317 | A1 | 6/2014 | Shturman | |
| 2016/0287285 | A1 | 10/2016 | Shturman | |
| 2019/0366041 | A1 | 12/2019 | Yang et al. | |
| 2020/0261111 | A1 | 8/2020 | Randall | |
| 2020/0345380 | A1 | 11/2020 | Boyle et al. | |

* cited by examiner 10
42
72
74
40
B
12
26
18
60
TS
14
Th
P
50
54
16
52
48
62

ATHERECTOMY CATHETERS HAVING MOVABLE BEADS

TECHNICAL FIELD

The present specification generally relates to atherectomy devices and, more specifically, atherectomy devices having abrasive beads movable along a core wire.

BACKGROUND

Traditional atherectomy devices include abrasive elements that can be rotated to perform an atherectomy procedure, such as abrading plaque in a patient's artery. These atherectomy devices fixedly couple the abrasive elements to a core wire such that rotation of the core wire rotates the abrasive elements with the core wire. However, these atherectomy devices require an additional mechanism for moving the abrasive element across the plaque. Accordingly, a need exists for improved atherectomy devices.

SUMMARY

In one embodiment, an atherectomy catheter for performing an atherectomy procedure, the atherectomy catheter includes a catheter body defining one or more lumens, a core wire extending through a core wire lumen of the one or more lumens of the catheter body, and an abrasive bead slidably mounted to the core wire. The core wire is configured to be coupled to an excitation device and operation of the excitation device causes the abrasive bead to rotate about and slide longitudinally along the core wire.

In another embodiment, an atherectomy assembly for performing an atherectomy procedure, the atherectomy assembly includes a catheter body defining one or more lumens, a core wire extending through a core wire lumen of the one or more lumens of the catheter body, an abrasive bead slidably mounted to the core wire, and an excitation device operatively coupled to the core wire and configured to vibrate the core wire. Vibration of the core wire causes the abrasive bead to rotate about and slide longitudinally along the core wire.

In yet another embodiment, a method of operating an atherectomy device, the method includes providing the atherectomy device, and activating an excitation device operatively coupled to a core wire to provide a vibration to the core wire, causing an abrasive bead to rotate about and slide longitudinally along the core wire. The atherectomy device includes a catheter body defining one or more lumens, the core wire extending through a core wire lumen of the one or more lumens of the catheter body, and the abrasive bead slidably mounted to the core wire.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein are directed to an atherectomy assembly including an atherectomy device and an excitation device. The atherectomy device may generally include a catheter body defining a plurality of lumens, a core wire extending through one of the lumens, an abrasive bead slidably mounted to the core wire, an excitation device operatively coupled to the core wire, and a pair of bumpers spaced apart along the core wire. The excitation device is configured to provide a vibration to the core wire. The vibrating core wire causes the abrasive bead to rotate and/or slide longitudinally along a length of the core wire. The abrasive bead is provided along the core wire between the bumpers 18 such that the bumpers 18 restrict the range of motion of the abrasive bead 16. Various embodiments of the atherectomy device 10 and the operation of the atherectomy device 10 will be described in more detail herein.

Figure 1:
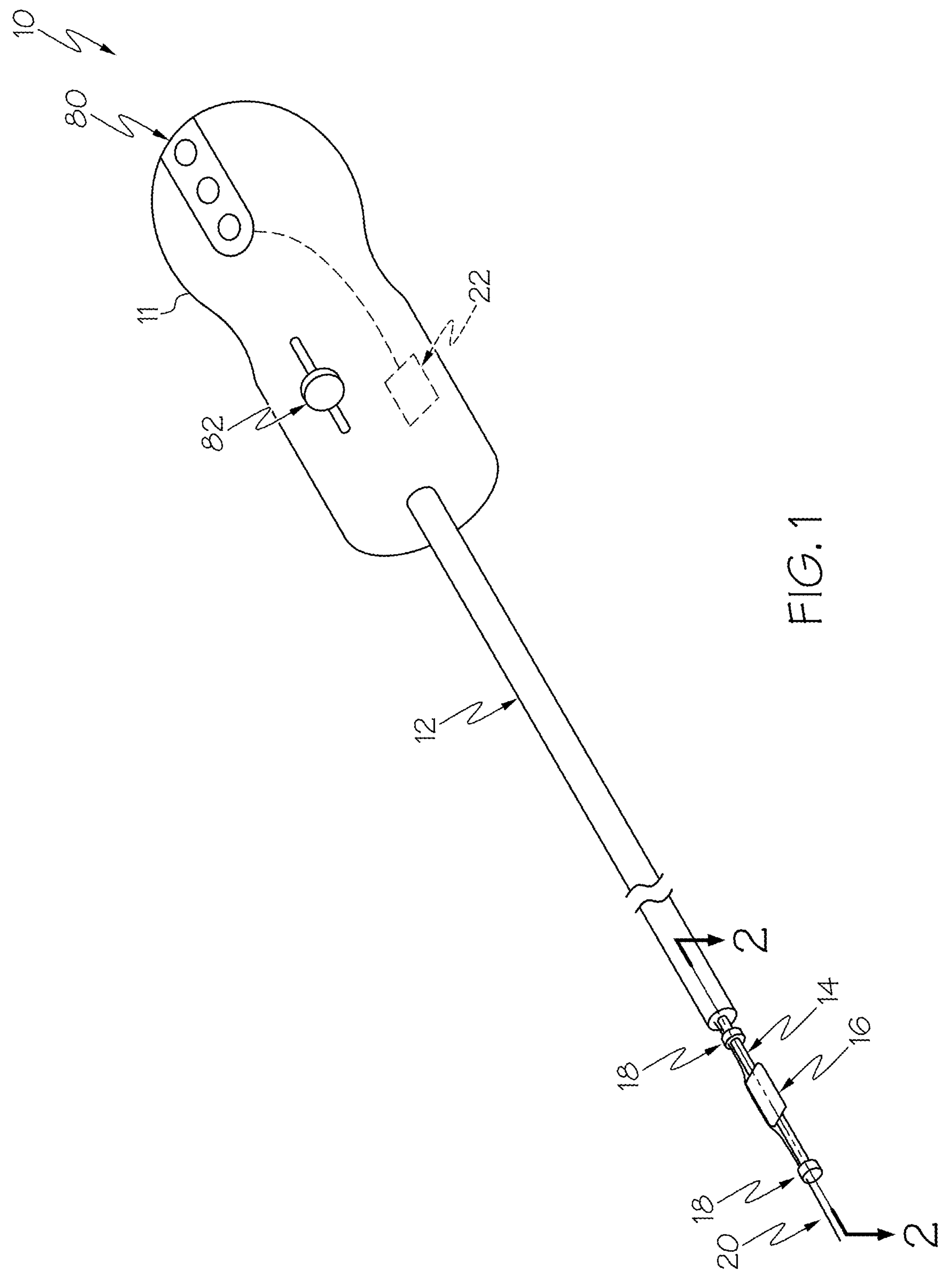
FIG. 1 schematically depicts a perspective view of an atherectomy device, according to one or more embodiments shown and described herein.
Figure 2:
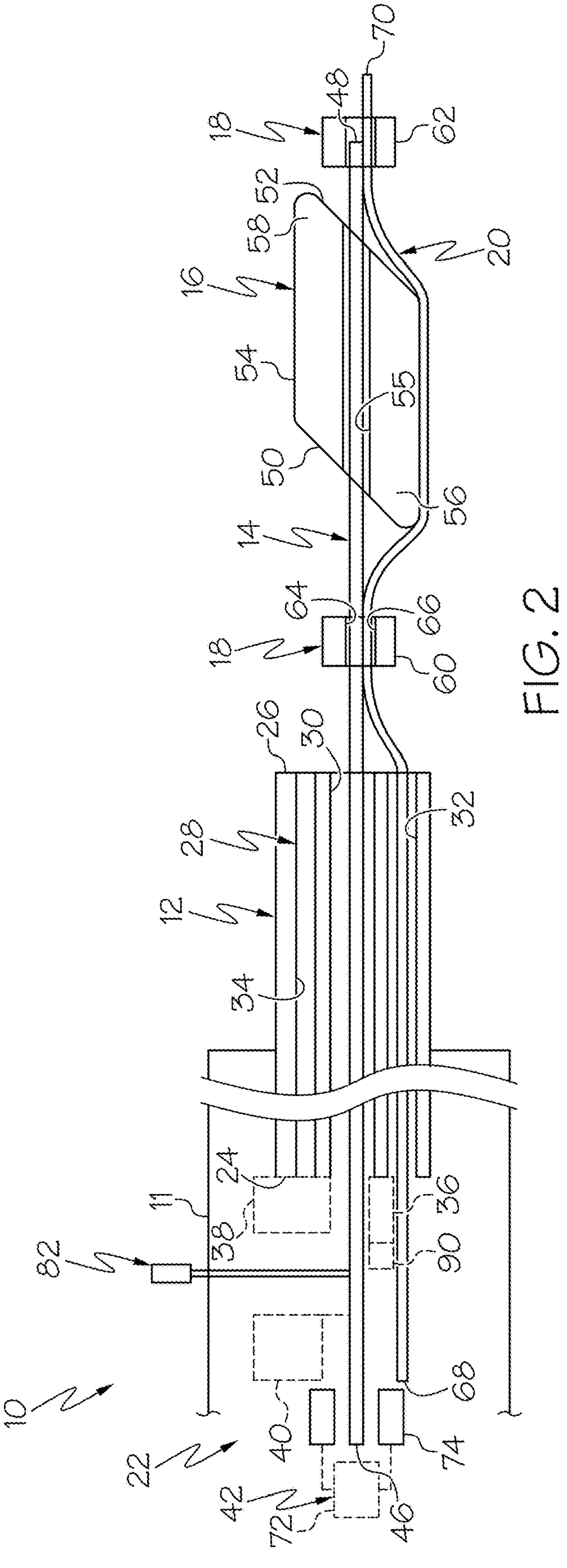
FIG. 2 schematically depicts a cross-sectional side view of the atherectomy device of FIG. 1 taken along line 2-2, according to one or more embodiments shown and described herein.

Referring now to FIGS. 1 and 2, an atherectomy device 10 for performing an atherectomy procedure on a patient's body is illustrated according to one or more embodiments described herein. The atherectomy device 10 may include a handle 11, a catheter body 12, a core wire 14, an abrasive bead 16, one or more bumpers 18, a guidewire 20, and a control system 22. The catheter body 12 may include a proximal end 24 and a distal end 26 opposite the proximal end 24. The proximal end 24 may be coupled to the handle 11, with the catheter body 12 extending from the handle 11 such that the distal end 26 of the catheter body 12 is spaced apart from the handle 11. The handle 11 may house the control system 22. The proximal end 24 of the catheter body 12 may be positioned within the handle 11 to operatively couple components of the control system 22 with the core wire 14 and the catheter body 12, as will be described in further detail below. The catheter body 12 may define one or more lumens 28 extending through the catheter body 12 from the proximal end 24 to the distal end 26. The one or more lumens 28 may include a core wire lumen 30, a guidewire lumen 32, and an aspiration lumen 34 that each extend in parallel with one another. Each of the one or more lumens 28 may be spaced apart from one another. However, it is contemplated and possible that any combination of the core wire lumen 30, the guidewire lumen 32, and the aspiration lumen 34 may be formed together, such that the lumen performs the function of each of the core wire lumen 30, the guidewire lumen 32, and the aspiration lumen 34.

Referring particularly to FIG. 2, the control system 22 may include a lubricant source 36, a vacuum source 38, an excitation device 40, a locking mechanism 42, and an input 80. Each of the components of the control system 22, including the lubricant source 36, the vacuum source 38, the excitation device 40, and the locking mechanism 42, may be positioned within the handle 11. However, in embodiments, the excitation device 40 may be separate from the control system 22 of the atherectomy device 10 where the atherectomy device 10 is configured to be operatively coupled to the excitation device 40 for operation of the atherectomy device 10. In such embodiments, the excitation device 40 may be positioned outside of the handle 11, and extend into the handle 11 to operatively couple to the core wire 14. The input 80 may be provided on an exterior of the handle 11 to allow a user to manipulate the input 80. As will be disclosed in further detail herein, the input 80 may be communicatively coupled to the other components of the control system 22 to operate those components.

The core wire lumen 30 may be configured to be fluidly coupled to the lubricant source 36 that provides lubricant through the core wire lumen 30 to the core wire 14 and the abrasive bead 16. The lubricant source 36 may include a pump 90 configured to move lubricant from the lubricant source 36 through the core wire lumen 30. The lubricant may reduce the friction between the abrasive bead 16 and the core wire 14 and/or between the abrasive bead 16 and the patient's body. The lubricant may be any traditional lubricant used in an atherectomy procedure. The aspiration lumen 34 may be configured to be fluidly coupled to the vacuum source 38 that provides suction through the aspiration lumen 34 in a distal to proximal direction. The distal to proximal direction is a direction extending from the distal end 48 of the core wire 14 toward the proximal end 46 of the core wire 14. The distal to proximal direction may similarly be referred to as the proximal direction. Similarly, the proximal to distal direction is a direction extending from the proximal end 46 of the core wire toward the distal end 48 of the core wire 14. The proximal to distal direction may similarly be referred to as the distal direction. The vacuum source 38 may be configured to aspirate abraded plaque particles into the aspiration lumen 34 at the distal end 26 of the catheter body 12 to remove the plaque particles from the patient's body. In embodiments, the vacuum source 38 may include a compartment (not shown) in fluid communication with the aspiration lumen 34 that collects and stores the abraded plaque particles.

The core wire 14 may include a proximal end 46 and an opposite distal end 48. The core wire 14 may extend through the core wire lumen 30 formed in the catheter body 12, with the proximal end 24 of the core wire 14 positioned outside of the core wire lumen 30 proximal to the proximal end 24 of the catheter body 12 and the distal end 26 of the core wire 14 positioned outside of the core wire lumen 30 distal to the distal end 26 of the catheter body 12. The core wire 14 may be operatively coupled to the excitation device 40 such that operation of the excitation device 40 vibrates the core wire 14. The core wire 14 may be movable along the core wire lumen 30 in the distal to proximal direction and the proximal to distal direction. The core wire 14 may be operatively coupled to the locking mechanism 42 such that the locking mechanism 42 may restrict movement of the core wire 14 when actuated. The locking mechanism 42 may be operatively coupled to the core wire 14 at a position proximal to the coupling between the excitation device 40 and the core wire 14 such that the locking mechanism 42 does not cause a reduction in vibration of the core wire 14 caused by the excitation device 40. The core wire 14 may be coated in a heat treated tubing to thermally insulate the core wire 14 from external temperatures and heat generated by operation of the atherectomy device 10.

The actuator 82 may extend from the handle 11 to be physically manipulatable by a user. The actuator 82 may be fixedly coupled to the core wire 14 and configured to move in the proximal and distal directions to move the core wire 14 in the proximal and distal directions. The actuator 82 may be any physical actuator that can be physically manipulated by a user, such as, for example, a toggle. Alternatively, the actuator 82 may be, for example, a linear actuator, a rotary actuator, a pneumatic actuator, or the like.

The abrasive bead 16 may include a proximal surface 50, a distal surface 52, and an abrasive surface 54. The abrasive surface 54 may be formed of any abrasive material capable of abrading plaque in a body lumen, such as, for example, a diamond coating. The abrasive surface 54 may extend in the proximal to distal direction between the proximal surface 50 and the distal surface 52. The abrasive bead 16 may define a channel 55 formed therein, with the core wire 14 extending through the channel 55 to movably couple the abrasive bead 16 to the core wire 14. The abrasive bead 16 may be configured to rotate and move along a length of the core wire 14. The channel 55 may extend through the abrasive bead 16 such that when the core wire 14 extends through the channel 55 in the abrasive bead 16 to movably couple the abrasive bead 16 to the core wire 14, the abrasive bead 16 is eccentrically disposed about the core wire 14. The abrasive bead 16 may be eccentrically disposed to cause eccentric rotation of the abrasive bead 16 about the core wire 14 when the excitation device 40 is activated. For example, the abrasive bead 16 may be eccentrically weighted with the center of gravity of the abrasive bead 16 offset, or spaced apart, from the core wire 14. For further example, the abrasive bead 16 may be eccentrically shaped, having a first portion 56 spaced apart from a second portion 58 along the proximal to distal direction, the first portion 56 having a center of gravity offset from the core wire 14, and the second portion 58 having a center of gravity offset from the core wire 14 and offset from the center of gravity of the first portion 56. In such example, the first portion 56 may be formed with the second portion 58 as a single monolithic piece, with the center of gravity of the entire abrasive bead 16 positioned along the core wire 14. For further example, the abrasive bead 16 may be eccentrically shaped as a slanted cylinder with the channel 55 extending through a geometric centerline of the abrasive bead 16. However, it is contemplated and possible that the channel 55 may be offset from the geometric centerline to provide an eccentric arrangement.

The channel 55 of the abrasive bead 16 may extend through the proximal surface 50 and the distal surface 52. The channel 55 may extend in parallel with the abrasive surface 54. However, in embodiments, the channel 55 may extend obliquely to the abrasive surface 54. In further embodiments, the channel 55 may extend perpendicular to the proximal surface 50 and the distal surface 52. The proximal surface 50 and the distal surface 52 may extend in parallel with one another, and may extend obliquely to the abrasive surface 54.

The one or more bumpers 18 may include a proximal bumper 60 and a distal bumper 62. Each of the bumpers 18 may define a core wire passage 64 and a guidewire passage 66 extending therethrough. The core wire 14 may extend through the core wire passage 64 of each of the proximal bumper 60 and the distal bumper 62 to fixedly couple the proximal bumper 60 and the distal bumper 62 to the core wire 14. The distal bumper 62 may be spaced apart from and positioned distal to the proximal bumper 60. The core wire 14 may be coupled to the bumpers 18 by, for example, adhesive, fasteners, epoxy, welding, press fit, or the like to restrict movement of the bumpers 18 relative to the core wire 14. In embodiments, the bumpers 18 may be movably coupled to the core wire 14 such that the position of the bumpers 18 may be adjusted, while preventing movement of the bumpers 18 when contacted by the abrasive bead 16 during operation of the atherectomy device 10. The guidewire passage 66 may be spaced apart from the core wire passage 64 and configured to receive the guidewire 20. The guidewire passage 66 may be sized greater than the guidewire 20 so that the guidewire 20 may be removed from the bumpers 18.

The proximal bumper 60 and the distal bumper 62 may be spaced apart by a travel length TL, the travel length TL being a length that the abrasive bead 16 may travel between the proximal bumper 60 and the distal bumper 62. The abrasive bead 16 may be positioned between the proximal bumper 60 and the distal bumper 62 such that the bumpers 18 restrict the travel length TL of the abrasive bead 16 along the core wire 14. The travel length TL may be adjusted by moving the position of the proximal bumper 60 and the distal bumper 62. The bumpers 18 may be formed of an elastic or other material such that the abrasive bead 16 is rebounded by the bumpers 18 when the abrasive bead 16 contacts the bumpers 18. For example, the bumpers 18 may be formed of rubber, springs, or the like.

Referring still to FIG. 2, the guidewire 20 may include a proximal end 68 and an opposite distal end 70. The guidewire 20 may extend through the guidewire lumen 32 formed in the catheter body 12. The proximal end 24 of the guidewire 20 may be positioned outside of the guidewire lumen 32 proximal to the proximal end 24 of the catheter body 12. The guidewire 20 may further extend from the handle 11 such that the proximal end 24 of the guidewire 20 may be manipulated by a user to remove the guidewire 20 from the bumpers 18 and the catheter body 12. The distal end 26 of the guidewire 20 may be positioned outside of the guidewire lumen 32 distal to the distal end 26 of the catheter body 12. The guidewire 20 may extend through the guidewire passage 66 of each of the bumpers 18 to movably couple the guidewire 20 to the bumpers 18, such that the guidewire 20 may be removable from the bumpers 18. The guidewire 20 may be configured to guide the atherectomy device 10 through the patient's body to the treatment site TS (FIG. 3A) and be removed from the catheter body 12 and the bumpers 18 once the atherectomy device 10 is positioned at the treatment site TS.

The excitation device 40 may be operatively coupled to the core wire 14 along the length of the core wire 14 between the proximal end 24 and the distal end 26. The excitation device 40 may be configured to vibrate the core wire 14 to cause the abrasive bead 16 to rotate and translate along the core wire 14. The excitation device 40 may vibrate the core wire 14 at a frequency capable of rotating and moving the abrasive bead 16 along the core wire 14. The frequency may be greater than 24 kHz, such as between 24 kHz and 30 kHz, and more particularly, 28 kHz. However, the excitation device 40 may vibrate the core wire 14 at any frequency capable of moving the abrasive bead 16 along the core wire 14. The frequency of the vibration from the excitation device 40 may be adjusted or selected by the user. The frequency may be increased to increase the rotational and translatable speed of the abrasive bead 16 along the core wire 14. Similarly, the frequency may be decreased to decrease the rotational and translatable speed of the abrasive bead 16 along the core wire 14. The excitation device 40 may be, for example, an ultrasonic transducer that supplies ultrasonic vibrations to the core wire 14.

The locking mechanism 42 may be configured to restrict the movement of the core wire 14 in the proximal and distal directions relative to the catheter body 12. Accordingly, once the catheter body 12 is located relative to the treatment site TS, the locking mechanism 42 may be actuated to lock the position of the core wire 14 relative to the treatment site TS. The locking mechanism 42 may be any traditional locking mechanism 42 for restricting movement of a core wire 14 relative to the catheter body 12, such as, for example, a clamp configured to clamp onto the core wire 14, thereby restricting movement of the core wire 14. The locking mechanism 42 may be positioned proximal to the coupling between the excitation device 40 and the core wire 14 so that the locking mechanism 42 does not interfere with the vibration of the core wire 14 caused by the excitation device 40. The locking mechanism 42 may include an actuator 72 and a clamp 74 operatively coupled to the actuator 72. The actuator 72 is configured to actuate the clamp 74 into contact with the core wire 14 to restrict movement of the core wire 14 in the distal and proximal directions. The locking mechanism 42 may be movable between a locked position and an unlocked position. In the locked position, the clamp 74 may be in contact with the core wire 14 such that the contact between the clamp 74 and the core wire 14 maintains the position of the core wire 14 with respect to the locking mechanism 42. In the unlocked position, the clamp 74 may be spaced apart from the core wire 14 so that the core wire 14 passes the locking mechanism 42 uninhibited. In the unlocked position, the core wire 14 may be movable in the longitudinal direction relative to the locking mechanism 42 and the catheter body 12.

Figure 3A:
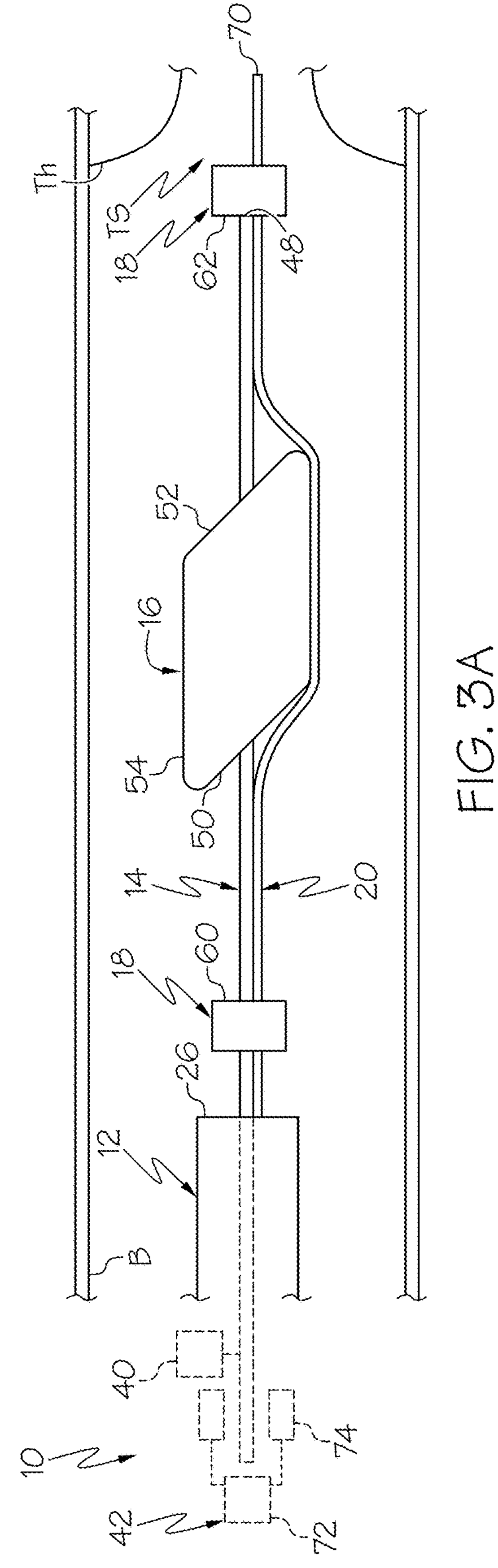
FIG. 3A schematically depicts a side view of the atherectomy device of FIG. 1 positioned in a body lumen of a patient, according to one or more embodiments shown and described herein.

Referring now to FIGS. 3A-3D, the operation of the atherectomy device 10 will now be described. The components of the atherectomy device 10 may be inserted into a body of a patient, particularly a body vessel B including the treatment site TS. The treatment site TS may be a site of a thrombus Th or other calcific plaque to be reduced or removed via the atherectomy procedure. The components of the atherectomy device 10 inserted into the body vessel B of the patient may include the catheter body 12, the core wire 14, the guidewire 20, the abrasive bead 16, the proximal bumper 60 and the distal bumper 62. Referring to FIG. 3A, the atherectomy device 10 is depicted positioned within the body vessel B, with the abrasive bead 16 spaced apart from the treatment site TS. The atherectomy device 10, particularly the core wire 14 and the abrasive bead 16, may be maneuvered through the body vessel B toward the treatment site TS using the guidewire 20 extending distal to the distal bumper 62. The core wire 14 may be moved in the proximal to distal direction away from or toward the catheter body 12 to position the abrasive bead 16 at the treatment site TS. The abrasive bead 16 may be positioned at the treatment site TS when the thrombus Th is positioned along the travel length TL between the proximal bumper 60 and the distal bumper 62.

Figure 3B:
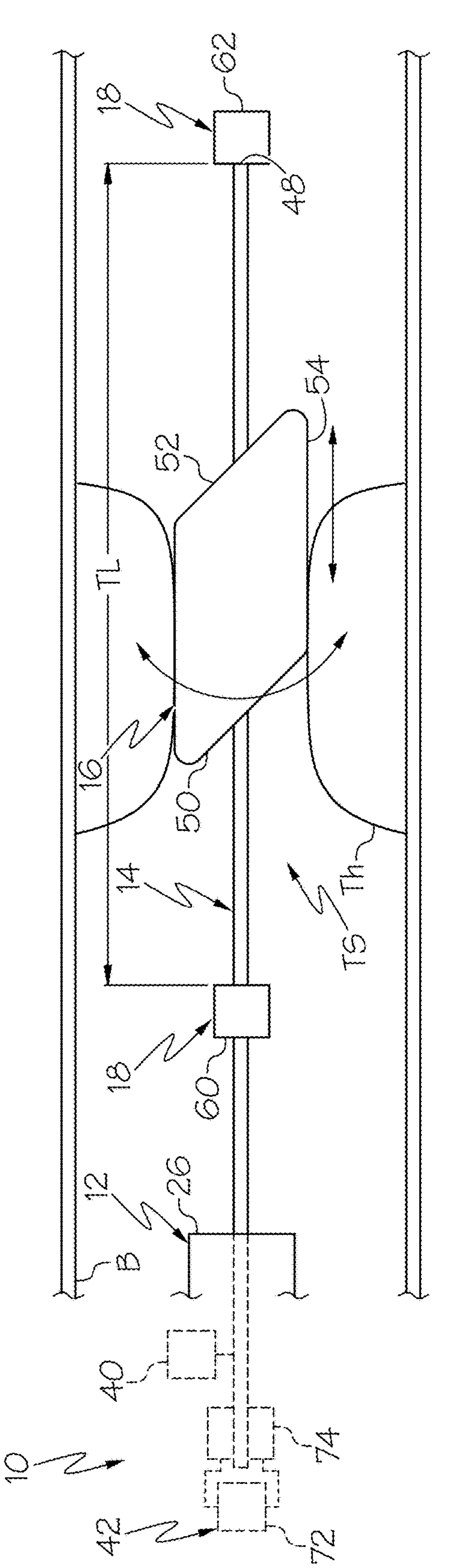
FIG. 3B schematically depicts a side view of the atherectomy device of FIG. 3A having an abrasive bead positioned at a treatment site, according to one or more embodiments shown and described herein.
Figures 3C, 3D:
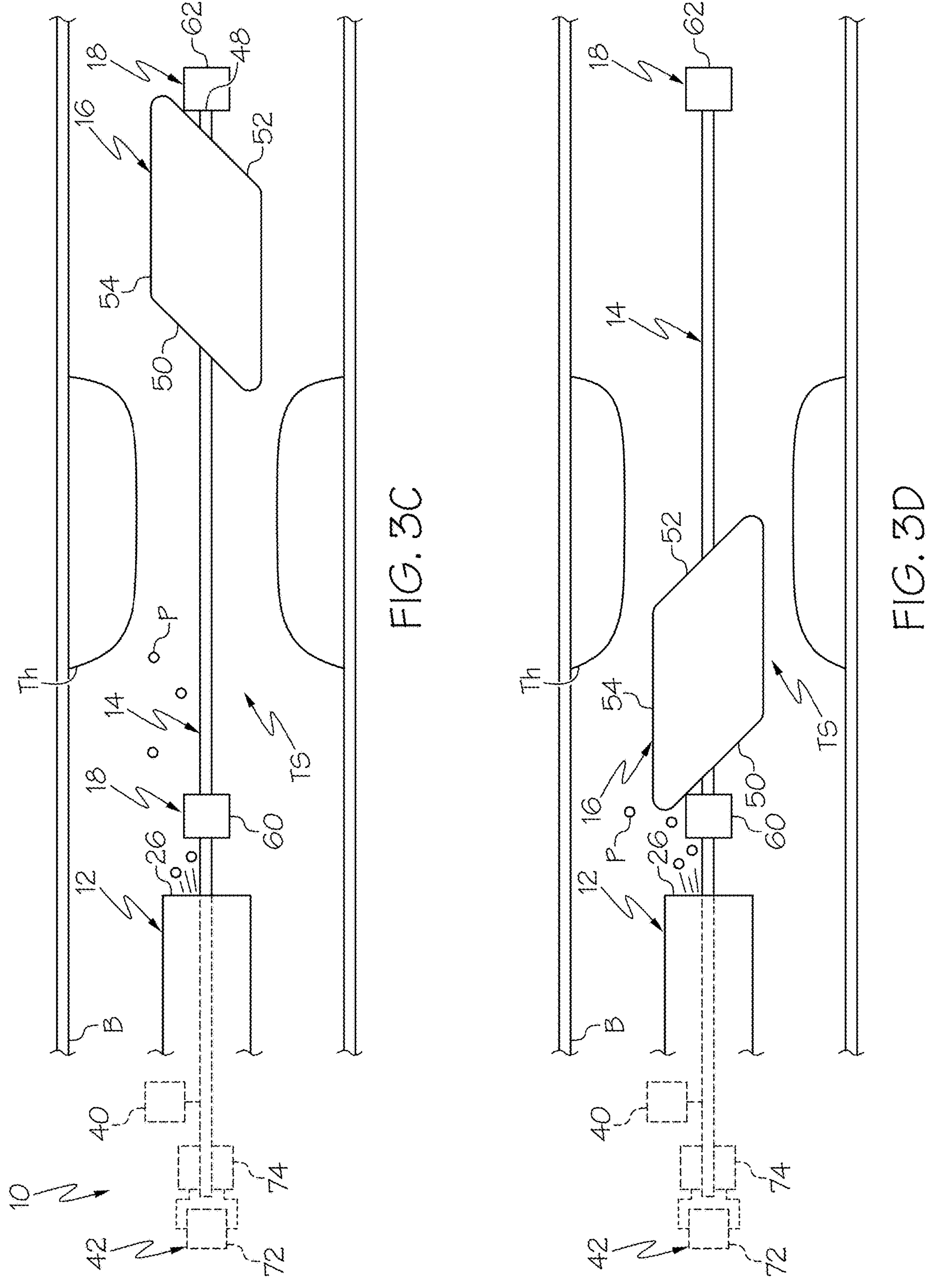
FIG. 3C schematically depicts a side view of the atherectomy device of FIG. 3A with the abrasive bead in a distal position, according to one or more embodiments shown and described herein.
FIG. 3D schematically depicts a side view of the atherectomy device of FIG. 3A with the abrasive bead in a proximal position, according to one or more embodiments shown and described herein.

Referring to FIG. 3B, once the abrasive bead 16 is positioned at the treatment site TS, the guidewire 20 may be retracted in the distal to proximal direction to remove the guidewire 20 from the body vessel B. The actuator 72 of the locking mechanism 42 may then be actuated to move the locking mechanism 42 from the unlocked position to the locked position, thereby restricting movement of the core wire 14 and maintaining the position of the abrasive bead 16 at the treatment site TS. When positioned at the treatment site TS, the abrasive bead 16 may be in a middle position, spaced apart from the proximal bumper 60 and the distal bumper 62. Once the locking mechanism 42 is in the locked position, the excitation device 40 may be activated to vibrate the core wire 14 to rotate and move the abrasive bead 16 along the travel length TL between the proximal bumper 60 and the distal bumper 62. When the abrasive bead 16 is moving along the travel length TL, the abrasive bead 16 moves between a distal position (FIG. 3C) and a proximal position (FIG. 3D). The middle position is positioned between the distal position and the proximal position.

Referring to FIG. 3C, when the abrasive bead 16 is in the distal position, the distal surface 52 of the abrasive bead 16 contacts the distal bumper 62. When moving from the middle position to the distal position, the contact between the abrasive bead 16 and the distal bumper 62 while the abrasive bead 16 is moving causes the abrasive bead 16 to rebound off of the distal bumper 62, redirecting the abrasive bead 16 away from the distal bumper 62 and back toward the middle position. The continued vibration of the core wire 14 from the excitation device 40 causes the abrasive bead 16 to move passed the middle position toward the proximal position.

Referring to FIG. 3D, when the abrasive bead 16 is in the proximal position, the proximal surface 50 of the abrasive bead 16 contacts the proximal bumper 60. When moving from the middle position to the proximal position, the contact between the abrasive bead 16 and the proximal bumper 60 while the abrasive bead 16 is moving causes the abrasive bead 16 to rebound off of the proximal bumper 60, redirecting the abrasive bead 16 away from the proximal bumper 60 and back toward the middle position. The continued vibration of the core wire 14 from the excitation device 40 causes the abrasive bead 16 to move passed the middle position again toward the distal position. The continued vibration of the core wire 14 causes the abrasive bead 16 to move between the distal position and the proximal position. While moving repeatedly between the distal position and the proximal position, the abrasive surface 54 of the abrasive bead 16 contacts the thrombus Th, thereby abrading and reducing the size of the thrombus Th. Particulate P from the abraded thrombus Th may be directed toward the aspiration lumen 34 due to suction caused by the vacuum source 38, so that the vacuum source 38 removes the particulate P from the body vessel B.

Figure 4:
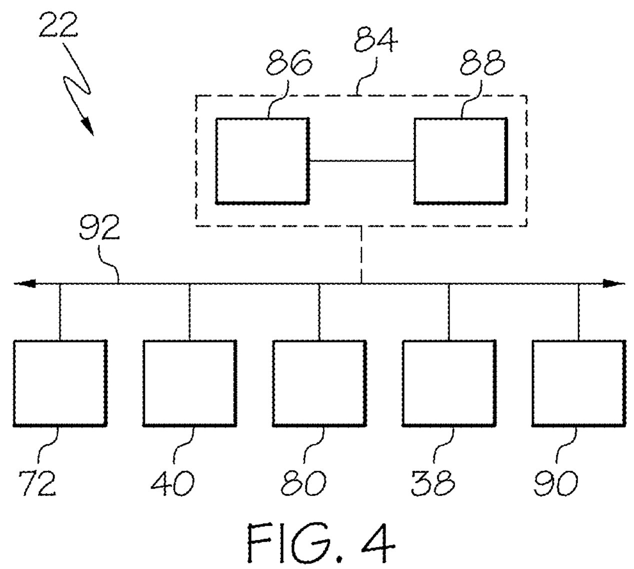
FIG. 4 schematically depicts a control system for operating the atherectomy device of FIG. 1, according to one or more embodiments shown and described herein.

Referring to FIG. 4, the control system 22 may further include a controller 84 communicatively coupled to the other components of the control system 22. The controller 84 may be communicatively coupled to the input 80, the actuator 72 of the locking mechanism 42, the excitation device 40, the vacuum source 38, and the pump 90 of the lubricant source 36 via a communication path 92. The controller 84 includes a processor 86 and a non-transitory electronic memory 88 to which various components are communicatively coupled. In some embodiments, the processor 86 and the non-transitory electronic memory 88 and/or the other components are included within a single device. In other embodiments, the processor 86 and the non-transitory electronic memory 88 and/or the other components may be distributed among multiple devices that are communicatively coupled. The controller 84 includes non-transitory electronic memory 88 that stores a set of machine-readable instructions. The processor 86 executes the machine-readable instructions stored in the non-transitory electronic memory 88. The non-transitory electronic memory 88 may comprise RAM, ROM, flash memories, hard drives, or any device capable of storing machine-readable instructions such that the machine-readable instructions can be accessed by the processor 86. Accordingly, the control system 22 described herein may be implemented in any conventional computer programming language, as pre-programmed hardware elements, or as a combination of hardware and software components. The non-transitory electronic memory 88 may be implemented as one memory module or a plurality of memory modules.

The processor 86 may be any device capable of executing machine-readable instructions. For example, the processor 86 may be an integrated circuit, a microchip, a computer, or any other computing device. The non-transitory electronic memory 88 and the processor 86 are coupled to the communication path 92 that provides signal interconnectivity between various components and/or modules of the actuation system. Accordingly, the communication path 92 may communicatively couple any number of processors with one another, and allow the modules coupled to the communication path 92 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 4, the communication path 92 communicatively couples the processor 86 and the non-transitory electronic memory 88 of the controller 84 with a plurality of other components of the control system 22. For example, the control system 22 depicted in FIG. 4 includes the processor 86 and the non-transitory electronic memory 88 communicatively coupled with the input 80, the actuator 72 of the locking mechanism 42, the excitation device 40, the vacuum source 38, and the pump 90 of the lubricant source 36.

The input 80 allows for a user to control operation of the other components of the control system 22. In some embodiments, the input 80 may be a switch, toggle, a plurality of buttons, or any combination of controls to provide user operation of the atherectomy device 10. As a non-limiting example, a user may actuate the atherectomy device 10 by operating the input 80. Actuation of the atherectomy device 10 may include any combination of: moving the locking mechanism 42 to the locked position, actuating the excitation device 40, actuating the pump 90 of the lubricant source 36, and actuating the vacuum source 38. The input 80 is coupled to the communication path 92 such that the communication path 92 communicatively couples the input 80 to other modules of the control system 22. The input 80 may provide a user interface for receiving user instructions as to a specific operating configuration of the atherectomy device 10.

Figure 5:
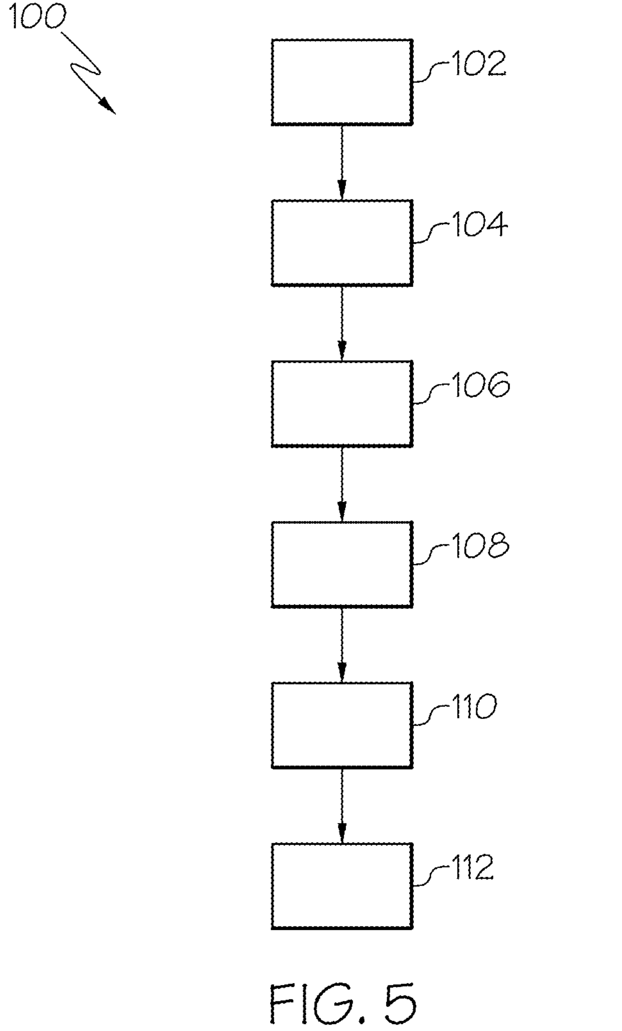
FIG. 5 depicts a flowchart of operating the atherectomy device of FIG. 1, according to one or more embodiments shown and described herein.

Referring now to FIG. 5, a flowchart of a method 100 of performing an atherectomy procedure is depicted. At step 102, the method 100 includes inserting the atherectomy device 10 into the patient's body, and advancing the atherectomy device 10 through the body lumen toward the treatment site TS. The guidewire 20 may guide the catheter body 12 through the body lumen. Once the atherectomy device 10 is positioned at the treatment site TS, at step 104, the method 100 may include moving the guidewire 20 in the distal to proximal direction to remove the guidewire 20 from the guidewire passages 66 in the bumpers 18 and the guidewire lumen 32 in the catheter body 12, thereby removing the guidewire 20 from the body vessel B. At step 106, the method 100 may include moving the catheter body 12 in the proximal to distal direction by manipulation of the actuator 82 to position the abrasive bead 16 at the treatment site TS. The core wire 14 may be positioned such that the plaque at the treatment site TS is positioned along the travel length TL between the bumpers 18. At step 108, the method 100 may include actuating the actuator 72 of the locking mechanism 42 to move the locking mechanism 42 into the locked position, thereby locking a position of the core wire 14 relative to the catheter body 12. The actuator 72 may be actuated by operation of the input 80. Locking the position of the core wire 14 may restrict longitudinal movement of the core wire 14 relative to the treatment site TS when the core wire 14 is vibrated by the excitation device 40.

At step 110, the method 100 may include activating the excitation device 40 to provide a vibration to the core wire 14. The excitation device 40 may be activated by operation of the input 80. The vibration of the core wire 14 causes the abrasive bead 16 to rotate about and slide along the core wire 14 between the proximal bumper 60 and the distal bumper 62. When the abrasive bead 16 contacts one of the bumpers 18, such as the distal bumper 62, the distal bumper 62 may redirect the abrasive bead 16, moving the abrasive bead 16 toward the proximal bumper 60. The movement of the abrasive bead 16 along the travel length TL causes the abrasive surface 54 to abrade the plaque at the treatment site TS. The lubricant source 36 may supply lubrication to the abrasive bead 16 along the core wire 14 to reduce friction between the abrasive bead 16 and the body lumen B and/or the thrombus Th. The abraded plaque may be in the form of particulate P in the body lumen B. The particulate P may be suctioned into the aspiration lumen 34 by the vacuum source 38 to remove the particulate P from the body lumen B. The vacuum source 38 and the lubricant source 36 may each be activated simultaneously with the excitation device 40 through operation of the input 80.

At step 112, the method 100 may include changing the frequency of vibration produced by the excitation device 40. The frequency of vibration may be increased to increase the longitudinal speed and rotational speed of the abrasive bead 16. The frequency of vibration may be decreased to decrease the longitudinal speed and rotational speed of the abrasive bead 16.

Figure 6:
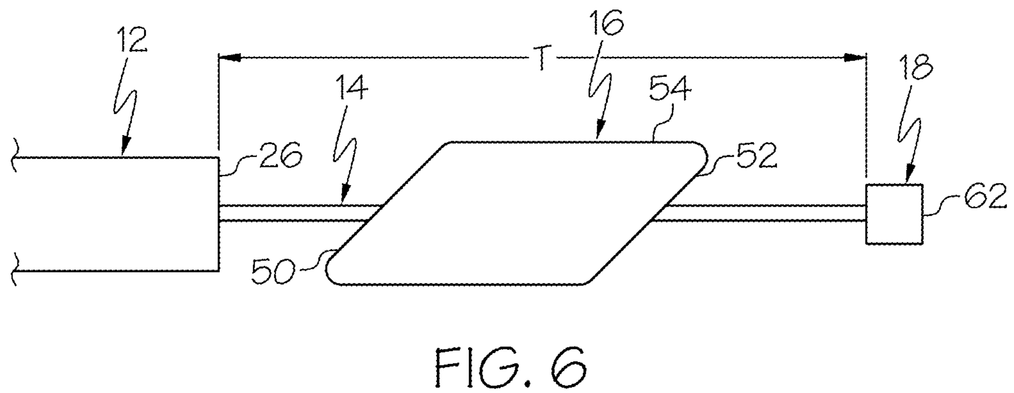
FIG. 6 schematically depicts another atherectomy device, according to one or more embodiments shown and described herein.

Referring now to FIG. 6, an alternative embodiment of the atherectomy device 10 is depicted. The alternative embodiment may only include the distal bumper 62 positioned distal to the abrasive bead 16, without the proximal bumper 60. In such embodiments, the abrasive bead 16 may rebound and travel between the distal bumper 62 and the catheter body 12 such that the travel length TL of the abrasive bead 16 may be restricted by the distal bumper 62 and the distal end 26 of the catheter body 12. The vibration of the core wire 14 from the excitation device 40 may cause the abrasive bead 16 to move in a single direction, such as the proximal to distal direction. In such case, the abrasive bead 16 may repeatedly move between the middle position and the distal position, where the abrasive bead 16 rebounds off of the distal bumper 62 when in the distal position to move the abrasive bead 16 back toward the middle position. The vibration of the core wire 14 may then move the abrasive bead 16 back to the distal position.

From the above, it is to be appreciated that defined herein is an atherectomy device including an abrasive bead movably coupled to a core wire and an excitation device operatively coupled to the core wire configured to vibrate the core wire. The vibration of the core wire causes the abrasive bead to rotate and move along a length of the core wire. The atherectomy device may further include a pair of bumpers coupled to the core wire with the abrasive bead positioned between the bumpers. The bumpers may restrict the travel length of the abrasive bead, where the abrasive bead may move between the pair of bumpers.

The following clauses also relate to the present disclosure:

1. An atherectomy catheter for performing an atherectomy procedure, the atherectomy catheter comprising: a catheter body defining one or more lumens; a core wire extending through a core wire lumen of the one or more lumens of the catheter body; and an abrasive bead slidably mounted to the core wire, wherein the core wire is configured to be coupled to an excitation device and operation of the excitation device causes the abrasive bead to rotate about and slide longitudinally along the core wire.

2. The atherectomy catheter according to clause 1, further comprising one or more bumpers disposed distal or proximal to the abrasive bead, the one or more bumpers are configured to restrict a travel length of the abrasive bead.

3. The atherectomy catheter according to clause 2, wherein the one or more bumpers comprise a first bumper positioned proximal to the abrasive bead and a second bumper positioned distal to the abrasive bead.

4. The atherectomy catheter according to clauses 2 or 3, wherein the one or more bumpers are formed of rubber.

5. The atherectomy catheter according to clauses 2 to 4, wherein the one or more bumpers comprise springs.

6. The atherectomy catheter according to clauses 2 to 5, further comprising a guidewire, wherein: the one or more lumens further comprise a guidewire lumen extending parallel to the core wire lumen; the one or more bumpers each comprise a guidewire passage formed therein; and the guidewire extends through the guidewire lumen and the one or more guidewire passages.

7. The atherectomy catheter according to any of the preceding clauses, wherein the core wire lumen is configured to be fluidly coupled to a lubricant source to provide lubricant along the core wire to the abrasive bead.

8. The atherectomy catheter according to any of the preceding clauses, wherein the one or more lumens comprises an aspiration lumen configured to be fluidly coupled to a vacuum source.

9. The atherectomy catheter according to any of the preceding clauses, wherein the core wire is coated with a heat treated tubing.

10. An atherectomy assembly for performing an atherectomy procedure, the atherectomy assembly comprising: a catheter body defining one or more lumens; a core wire extending through a core wire lumen of the one or more lumens of the catheter body; and an abrasive bead slidably mounted to the core wire, and an excitation device operatively coupled to the core wire and configured to vibrate the core wire, wherein vibration of the core wire causes the abrasive bead to rotate about and slide longitudinally along the core wire.

11. The atherectomy assembly according to clause 10, wherein the excitation device is an ultrasonic transducer that supplies ultrasonic vibrations to the core wire.

12. The atherectomy assembly according to clauses 10 or 11, further comprising one or more bumpers disposed distal or proximal to the abrasive bead, the one or more bumpers are configured to restrict a travel length of the abrasive bead.

13. The atherectomy assembly according to clause 12, wherein the one or more bumpers comprise a first bumper positioned proximal to the abrasive bead and a second bumper positioned distal to the abrasive bead.

14. The atherectomy assembly according to clauses 12 or 13, further comprising a guidewire, wherein: the one or more lumens further comprise a guidewire lumen extending parallel to the core wire lumen; the one or more bumpers each comprise a guidewire passage formed therein; and the guidewire extends through the guidewire lumen and the one or more guidewire passages.

15. The atherectomy assembly according to clauses 10 to 14, wherein the core wire lumen is configured to be fluidly coupled to a lubricant source to provide lubricant along the core wire to the abrasive bead.

16. The atherectomy assembly according to clauses 10 to 15, wherein the one or more lumens comprises an aspiration lumen configured to be fluidly coupled to a vacuum source.

17. The atherectomy assembly according to clauses 10 to 16, wherein the core wire is coated with a heat treated tubing.

18. A method of performing an atherectomy procedure, the method comprising: advancing an atherectomy catheter through a body lumen to a treatment site, the atherectomy catheter comprising: a catheter body defining one or more lumens; a core wire extending through a core wire lumen of the one or more lumens of the catheter body; and an abrasive bead slidably mounted to the core wire; and activating an excitation device operatively coupled to the core wire to provide a vibration to the core wire, causing the abrasive bead to rotate about and slide longitudinally along the core wire.

19. The method according to clause 18, further comprising locking a position of the core wire to restrict longitudinal movement of the core wire relative to the treatment site.

20. The method according to clauses 18 or 19, further comprising changing a frequency of the vibration produced by the excitation device.

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

The invention claimed is:

1. An atherectomy catheter for performing an atherectomy procedure, the atherectomy catheter comprising:

a catheter body defining one or more lumens;

a core wire extending through a core wire lumen of the one or more lumens of the catheter body; and an abrasive bead slidably mounted to the core wire, wherein the core wire is configured to be coupled to an excitation device and operation of the excitation device causes the abrasive bead to rotate about and slide longitudinally along the core wire.

2. The atherectomy catheter of claim 1, further comprising one or more bumpers disposed distal or proximal to the abrasive bead, the one or more bumpers are configured to restrict a travel length of the abrasive bead.

3. The atherectomy catheter of claim 2, wherein the one or more bumpers comprise a first bumper positioned proximal to the abrasive bead and a second bumper positioned distal to the abrasive bead.

4. The atherectomy catheter of claim 2, wherein the one or more bumpers are formed of rubber.

5. The atherectomy catheter of claim 2, wherein the one or more bumpers comprise springs.

6. The atherectomy catheter of claim 2, further comprising a guidewire, wherein:

the one or more lumens further comprise a guidewire lumen extending parallel to the core wire lumen;

the one or more bumpers each comprise a guidewire passage formed therein; and the guidewire extends through the guidewire lumen and the one or more guidewire passages.

7. The atherectomy catheter of claim 1, wherein the core wire lumen is configured to be fluidly coupled to a lubricant source to provide lubricant along the core wire to the abrasive bead.

8. The atherectomy catheter of claim 1, wherein the one or more lumens comprises an aspiration lumen configured to be fluidly coupled to a vacuum source.

9. The atherectomy catheter of claim 1, wherein the core wire is coated with a heat treated tubing.

10. An atherectomy assembly for performing an atherectomy procedure, the atherectomy assembly comprising:

a catheter body defining one or more lumens;

a core wire extending through a core wire lumen of the one or more lumens of the catheter body;

an abrasive bead slidably mounted to the core wire, and an excitation device operatively coupled to the core wire and configured to vibrate the core wire, wherein vibration of the core wire causes the abrasive bead to rotate about and slide longitudinally along the core wire.

11. The atherectomy assembly of claim 10, wherein the excitation device is an ultrasonic transducer that supplies ultrasonic vibrations to the core wire.

12. The atherectomy assembly of claim 10, further comprising one or more bumpers disposed distal or proximal to the abrasive bead, the one or more bumpers are configured to restrict a travel length of the abrasive bead.

13. The atherectomy assembly of claim 12, wherein the one or more bumpers comprise a first bumper positioned proximal to the abrasive bead and a second bumper positioned distal to the abrasive bead.

14. The atherectomy assembly of claim 12, further comprising a guidewire, wherein:

the one or more lumens further comprise a guidewire lumen extending parallel to the core wire lumen;

the one or more bumpers each comprise a guidewire passage formed therein; and the guidewire extends through the guidewire lumen and the one or more guidewire passages.

15. The atherectomy assembly of claim 10, wherein the core wire lumen is configured to be fluidly coupled to a lubricant source to provide lubricant along the core wire to the abrasive bead.

16. The atherectomy assembly of claim 10, wherein the one or more lumens comprises an aspiration lumen configured to be fluidly coupled to a vacuum source.

17. The atherectomy assembly of claim 10, wherein the core wire is coated with a heat treated tubing.

18. A method of operating an atherectomy device, the method comprising:

providing the atherectomy device that comprises:

a catheter body defining one or more lumens;

a core wire extending through a core wire lumen of the one or more lumens of the catheter body; and an abrasive bead slidably mounted to the core wire; and activating an excitation device operatively coupled to the core wire to provide a vibration to the core wire, causing the abrasive bead to rotate about and slide longitudinally along the core wire.

19. The method of claim 18, further comprising locking a position of the core wire to restrict longitudinal movement of the core wire relative to the catheter body.

20. The method of claim 19, further comprising changing a frequency of the vibration produced by the excitation device.

* * * * *